Figure 1:
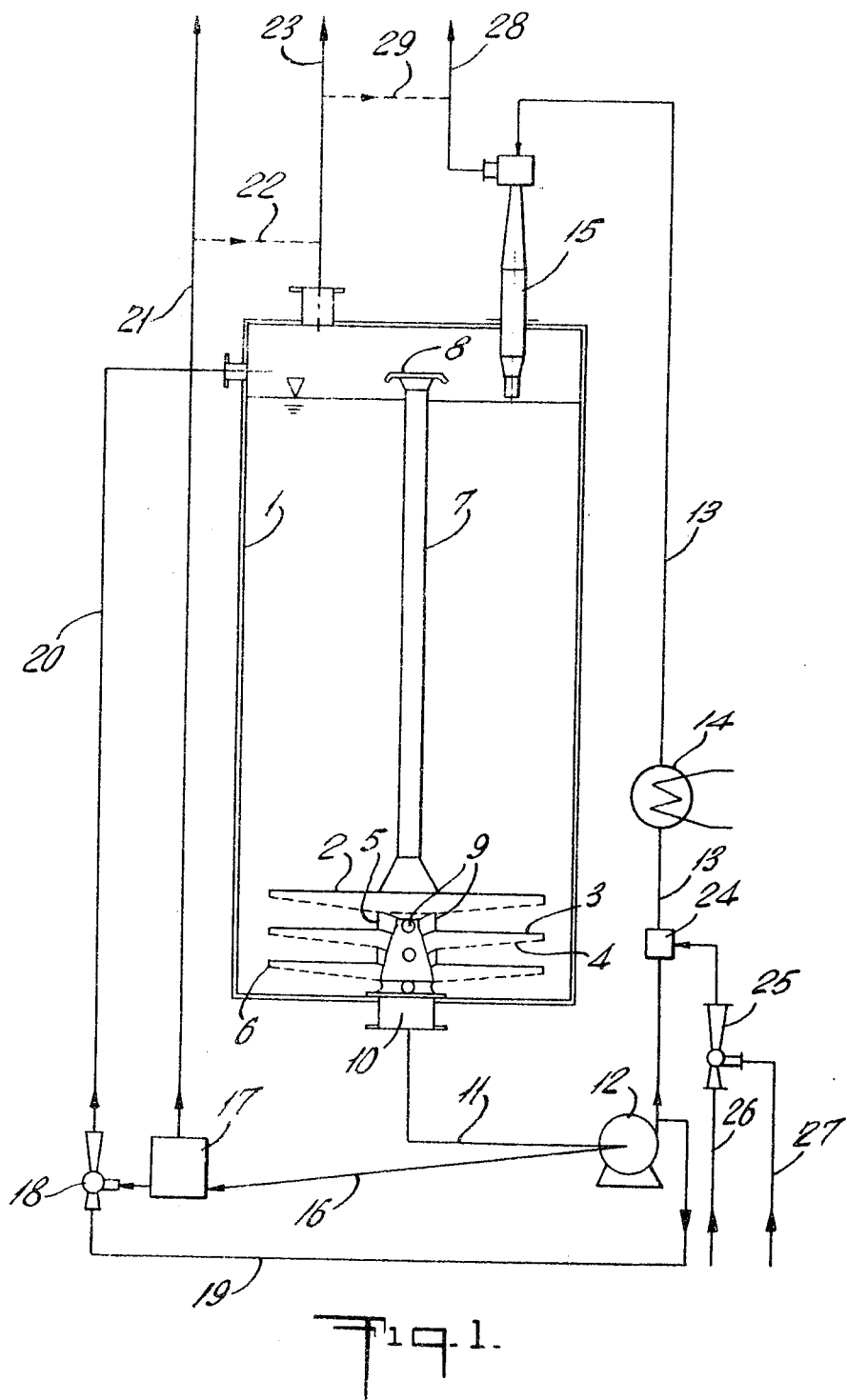

United States Patent [19] [11] 3,945,922
Jagusch et al. [45] Mar. 23, 1976

[54] INSTALLATION FOR CHARGING LIQUIDS, PARTICULARLY FERMENTATION LIQUIDS, WITH GAS

[75] Inventors: Leonhard Jagusch, Leipzig; Werner Schonherr, Neukieritzsch, both of Germany

[73] Assignee: VEB Chemieanlagenbau-und Montegekombinat, Leipzig, Germany

[22] Filed: June 20, 1974

[21] Appl. No.: 481,078

[52] U.S. Cl............. 210/195 R; 210/196; 210/199; 210/202; 210/218; 210/220; 55/87
[51] Int. Cl.²..................... C02C 5/04; B01D 47/00
[58] Field of Search....... 55/52, 184, 186, 199, 200, 55/201, 203, 87, 178, 193; 195/142; 210/14, 15, 63, 195, 221, 194, 196, 199, 202, 209, 218, 220; 261/36 R, DIG. 19, DIG. 75

[56] References Cited
UNITED STATES PATENTS

| | | | |
|---|---|---|---|
| 2,291,138 | 7/1942 | Blom | 55/199 |
| 2,379,133 | 6/1945 | Curtis | 55/199 |
| 3,114,677 | 12/1963 | Stich | 195/142 |
| 3,201,327 | 8/1965 | Beck | 195/142 X |
| 3,228,526 | 1/1966 | Ciabattari et al. | 210/221 |
| 3,271,304 | 9/1966 | Valdespino et al. | 210/14 X |
| 3,717,552 | 2/1973 | Hondermarck et al. | 195/142 |
| 3,834,133 | 9/1974 | Bow | 261/36 R X |

Primary Examiner—Charles N. Hart
Assistant Examiner—Robert H. Spitzer
Attorney, Agent, or Firm—Nolte and Nolte

[57] ABSTRACT

Installation for gassing highly emulsified fermentation liquids in which liquid recirculated to the reaction vessel is gassed in a centrifugal pump to improve the efficiency of the process.

14 Claims, 3 Drawing Figures

INSTALLATION FOR CHARGING LIQUIDS, PARTICULARLY FERMENTATION LIQUIDS, WITH GAS

The invention concerns an installation for charging liquids with gas, and in particular, for the intensive charging with gas of strongly emulsifying fermentation liquids.

A type of installation is known, which consists of a reaction vessel, a centrifuge and a gas-charging device that are connected with each other by pipe lines, and which is used for carrying out a recirculating gas-charging process.

The liquid, which is charged with the gases generated in the reaction, is degassed in the centrifuge. The degassed liquid is pumped into the reactive vessel by means of the centrifuge via a water-jet pump, where it sucks in fresh air. The gas liberated in the centrifuge escapes into the atmosphere.

The application of this known type of plant on a large scale takes a great amount of apparatus, as in the recirculating gas-charging process large amounts of liquid of several hundred to several thousand cubic meters per hour must be pumped and known pump centrifuges have only small rated outputs.

The centrifuge ensures thorough degassing of the circulated liquid, but the power required to pump liquids is very large in comparison with centrifugal pumps.

In another known aeration apparatus, in which the liquid is pumped through an external cooling circuit by means of centrifugal pumps, a decanting vessel is arranged inside or outside the reactor. The centrifugal pumps draw off partially degassed liquid from the decanting vessel, whereby an improvement of the hydraulic efficiently is achieved. However, this known technical solution is not economically applicable for intensive gas-charging, as the advantage of the high volume-time yields in the active reaction chamber is cancelled by the large volume of the required decanting vessel.

In a further known recirculating gas-charging arrangement so-called well inflows, which make possible a multi-story arrangement of the reaction chambers, are used for generating highly turbulent, gas-containing liquid jets. However, due to the simple central opening provided for the admission of gas at the entrance to the well, the most favorable conditions do not exist for achieving a homogeneous jet with very fine gas dispersion at the well exit, as is required for optimum introduction of the gas. Moreover, with a multi-story arrangement of the reaction chambers the flow conditions in the lowest story are different from those in the reaction chambers on top of it. In the lower story, the circulated stream flows off from the bottom of the reactor, while the gas-charged medium flows off into the well inflows only from the surface in the upper stories, so that to the uplift motion due to the gas bubbles is further added an additional flow component, which leads to a shortening of the dwelling time of the gas bubbles in the liquid. The homogeneity and thus, the condition for optimal introduction of the gas, is worse in the upper stories than in the lowest story.

It is the purpose of the invention to eliminate the disadvantages found in the present state of the art and to make thereby possible high material-transfer velocities even in strongly emulsifying liquids with low energy consumption.

It is an object of the invention to create an installation for charging liquids with gas, and in particular, for the intensive charging with gas of strongly emulsifying liquids, which prior to the gas-charging largely degassed the circulating liquid with a minimum requirement as to energy and machinery and thereby optimally increases the driving force for the transfer of matter, improves the efficiency of the circulating pumps when pumping strongly emulsifying liquids, ensures intensive material exchange in the entire available reaction space, makes possible, if required, maximum utilization of the gas component to be entered from gas mixtures with a minimum expenditure of energy, as well as creates better conditions for homogeneous gas-charging with fine bubbles of the entire reaction space.

According to the invention, the problem is solved by the provision that the charging with gas of liquids, particularly of strongly emulsifying fermentation liquids, is performed in an installation consisting of a reaction vessel, known per se, of one or several stories, in whose lower part, centrally above a suction line starting at the bottom, gas separator with a foam exhaust line which is equipped with a throttling device and leads above the liquid surface of one of the stories of the reaction vessel, is arranged; one or several degassing centrifugal pumps, whose venting line leads to a liquid separator, at the lower part of which one or several liquid pumping members are arranged which are connected with the reaction vessel via a return line; as well as of vertically disposed gas-charging devices, known per se, which generate gas-liquid jets and end in the reaction vessel above the liquid surface.

Utilizing gravity, the larger gas bubbles contained in the circulating liquid are separated out in the gas separator. These gas bubbles are returned via the foam exhaust line. The throttling device in the foam exhaust line serves to adjust an optimal mode of operation of the gas separator. The predegassed liquid flows via the intake line to the degassing centrifugal pumps. Using the centrifugal forces occurring in the rotor, further degassing of the circulating liquid takes place in these centrifugal pumps. In this process, the smaller, already highly utilized gas bubbles, which inhibit the gas exchange process, are separated out in the vicinity of the hub in the channels of the centrifugal pump rotor.

The gas containing droplets of liquid is fed from the channels of the centrifugal pump rotor, via the gas exhaust line, to the liquid separator, which is provided with a gas exhaust line. The liquid precipitated in the liquid separator is pumped back into the fermentor via the return line by means of the pumping equipment following the separator. The liquid, which has now been degassed to a very high degree using gravity and the centrifugal forces in the rotors of the centrifugal pumps, is fed by the latter, via the pump line for charging the reactor contents with gas, to the gas charging devices, known per se, which generates gas-liquid jets. With this solution according to the invention is achieved that without additional consumption of energy, finely distributed gas, which is strongly depleted of components which are used up, for instance, in fermentation processes, and which is enriched heavily with the gas that is produced, for instance, in fermentation, is very largely removed from the liquid, so that the partial pressure difference for the transfer of matter is increased and the conditions for the absorption of very fine bubbles of fresh gas by the liquid is improved. Furthermore, the hydraulic efficiency is substantially improved in the degassing centrifugal pumps. The power required for the pump for recirculating the liquid produced in the liquid separator, which is very small in comparison with the main circulating pump, is negligible in view of the power savings due to the higher hydraulic efficiency of the main circulating pump.

The gas separator consists, according to the invention, of alternatingly arranged disc-shaped guidance devices and conical guidance devices provided with holes or slits, which are alternatingly connected inside and outside by cylindrical spacers. The liquid charged with gas in the reactor flows here through the interspaces of the guidance devices from the outside to the inside. The flow velocity is made here so that the larger gas bubbles separate from the gas-containing liquid upward due to the force of gravity. These gas bubbles flow through the conical guidance devices provided with holes or slits toward the foam exhaust line which adjoins the guidance devices centrally. The pre-degassed liquid flows over the disc-shaped guidance devices and through radially arranged collecting canals to a manifold which is centrally arranged in the reaction vessel and to which the intake line of the centrifugal pump is connected.

Another embodiment of the gas separator consists, according to the invention, of conical guidance devices composed of individual segments. The flow velocity between the guidance devices is likewise chosen so that the larger gas bubbles can separate from the gas-containing liquid upward due to gravity. The larger gas bubble separated from the gas-containing liquid flow radially in the upper part of the spaces formed by the guidance devices inward to the foam exhaust line which is connected centrally to the topmost conical guidance device. The pre-degassed liquid flows radially from the inside out against the entering-flow direction due to the conical guidance device and the force of gravity, is caught in collecting pockets and gets from there through openings into cavities formed by the individual segments of the guidance devices. From these cavities the pre-degassed liquid flows between the lowest conical guidance device and the bottom of the vessel to the intake line of the degassing centrifugal pump.

The liquid produced in the liquid separator is pumped back, according to the invention, into the reaction vessel, preferably by means of a water-jet pump, whose driving jet connection is connected via a connecting line with the output line of the degassing centrifugal pump. Thus, no additional drive with moving parts is necessary for the solution according to the invention.

According to the invention, a preliminary gas-charging device can be arranged in the output line after the degassing centrifugal pump. Through this gas-charging, the circulation volume is prepared for an intensive gas exchange process. Thus, fresh gas is continuously fed-in in the reaction vessel and in the circulating flow to all of the liquid, whereby maximum gas transfer is ensured. Feeding-in the gas after the degassing centrifugal pump furthermore reduces the pump pressure required, due to the decrease in the density of the circulating flow mass. Thereby, the energy required for circulating a given quantity of liquid becomes less. According to the invention, there can be arranged ahead of the preliminary gas-charging device a jet device, to whose driving jet input a driving gas line is connected and to whose suction connector a gas supply line is connected, whose pressure outlet is connected with the preliminary gas-charging device, so that the energy of a gas under high pressure can be utilized. A heat exchanger can be arranged in the pump line, according to the invention, for the removal of the often considerable amounts of reaction heat which is liberated in the gas-charging of liquids.

According to the invention, the exhaust gas line of the liquid separator can be connected with the central exhaust gas line of the reaction vessel.

If maximum utilization of the gas is desired, the central exhaust gas line of the reaction vessel is connected, according to the invention, with the fresh-gas supply line of the gas-charging device. It is thereby possible to use the gas escaping at the liquid surface in the reaction vessel or the gas coming from the gas separator again completely or partly by automatic suction through the gas-charging devices for charging the liquid in the reaction vessel with gas. In a further embodiment for high gas utilization, the central exhaust gas line of the reaction vessel is connected, according to the invention, with the fresh-gas supply line of the gas-charging device, the exhaust line of the liquid separator leading from the installation system separately. The gas discharged via the central exhaust gas line can be used over again completely or partly by automatic suction through the gas-charging device for charging the liquid in the reaction vessel with gas. Fresh gas is fed in here completely or partly in the preliminary gas-charging device or in the gas-charging device. Exhaust gas is discharged only from the degassing centrifugal pump. This exhaust gas is maximally utilized.

Well inflow devices are preferably used as the gas-charging devices. The well inflows consist of a preferably vertical well pipe and a well head. At the entrance to the well pipe an initial gas distribution device in the form of several circular, oval, tear-shaped or triangular gas supply ducts is arranged. These gas supply canals are uniformly distributed over the entire entrance cross section of the well pipe. The contact area between the liquid and the intake gas at the entrance of the well pipe can thereby be enlarged as much as desired. Therefore, the entire length of the well pipe is available over the entire cross section for the dispersion of the gas in the liquid and one has completely homogeneous gas-liquid jet at the exit from the well pipe. If the reaction spaces are arranged in several stores, the lower well inflows are equipped, according to the invention, with a cylindrical skirt for feeding-in the major part of the circulating liquid from the bottom of the reaction vessel and with an inlet funnel to let the foam flow off, as well as with means for adjusting the inlet cross sections. By feeding the major part of the circulating liquid from the bottom of the reaction vessel, the flow conditions in the upper stories are matched to the flow conditions in the lower story, where the liquid is drawn from the bottom of the basin by the degassing centrifugal pump. Thereby, better homogeneity in the reaction vessel is assured and the dwelling time of the gas bubbles in the liquid is also extended. The inlet funnel makes sure that the foam generated can be led off to the story below. By the means for adjusting the size of the inlet cross sections one can, on the one hand, control the amount of foam flowing off and, on the other hand, it is ensured that no spent gas located above the gas-charged liquid, is sucked in, but only gas via the fresh-gas supply from the well overflow is brought into the story below.

With the solution according to the invention it is possible to increase the mean partial pressure of the gas component to be introduced into the liquid substantially and thereby, the driving force for the gas transfer. In addition, the hydraulic efficiency of the centrifugal pumps is increased substantially. Moreover, the solution found by pre-charging the circulating flow with gas makes possible intensive utilization of the circulating volume. As the circulating volume of the loop can be as much as 25 percent of the volume of the reaction vessel, a substantial increase of the total gas charge results therefrom. On the other hand, the conditions for fine dispersion of the gas in the exit jet and for homogeneity in the entire working volume of multi-story reactors are substantially improved at the known well inflow devices by the measures according to the invention. Thereafter, the solution according to the invention makes possible overall to realize considerably higher specific gas transfer velocities as compared to the state of the art, with lower energy and investment costs for the gas transfer. The following comparison of specific performance characteristics of the more important circulating gas charging equipments, for instance, for use in carbohydrate yeast fermentation on a technical scale will illustrate this:

The pre-degassed liquid flows to the degassing centrifugal pump 12 via radially disposed collecting canals 9, a manifold 10 centrally attached in the reaction vessel 1 and the intake line 11. The centrifugal pump 12 pumps the liquid via the output line 13 and the heat exchanger 14 to the liquid-gas jet device 15. The circulated liquid is at the same time further degassed in the centrifugal pump 12, utilizing the centrifugal forces occurring in its rotor. The gas, which contains drops of liquid and which is separated out in the rotor of the centrifugal pump 12, is fed to a liquid separator 17 via the venting line 16, which begins in the canal near the hub of the centrifugal pump rotor. The liquid collected in the liquid separator 17 is pumped back by the water-jet pump 18, which is operated with liquid from the pump output line 13 via the connecting line 19, into the reaction vessel 1 via the return line 20. The gas produced in the liquid separator 17 is discharged into the ambient atmosphere via the exhaust gas line 21 or into the central exhaust gas line 23 via the connecting line 22. The liquid in the circulation loop is charged with gas in the preliminary gas-charging device 24 disposed between the centrifugal pump 12 and the heat ex-

| Gas-Charging Equipment | Volume-Time Yield in kg HTS/t h | | Specific Energy Requirement in kWh/kg HT | |
|---|---|---|---|---|
| Rieche Revolving Vat | 2 to | 3 | 0.45 to | 1.0 |
| Waldholf Vat | 1 | 1.8 | 0.8 | 2.3 |
| Lafrancois Vat | 2 | 3 | 0.45 | 0.8 |
| Installation according to the invention | 10 | 15 | 0.3 | 0.4 |

In addition, high utilization of the gas, if desired, is possible simply and very economically by the circulating mode of operation of the gas to be charged.

The invention will be explained in the following in further detail with reference to two examples of embodiments. In the attached drawings is shown, in FIG. 1, a side view of an embodiment according to the invention, FIG. 2, a side view of a further embodiment according to the invention, and in FIG. 3, a cross section A—A as per FIG. 2.

In the embodiment of the invention shown in FIG. 1, the strongly emulsified liquid flows from the reaction vessel 1 to a gas separator 2 centrally located in the lower part above the bottom, where it is conducted from the outside to the inside through the interspaces of several conical and disc-shaped guidance devices 3 and 4, which are stacked on top of each other and are connected by cylindrical spacers 5 and 6. This strongly emulsified liquid is separated into an emulsion with a high gas content and into a pre-degassed liquid. The emulsion with a high gas content flows through the conical guidance devices 4, provided with holes, toward the foam exhaust line 7, which is equipped with a throttling device 8 at its upper end. The throttling device 8 may be provided with a setting device for changing the exit cross section. The emulsion with high gas content which leaves the throttling device 8 with overpressure caused by the difference in density in the reaction vessel 1 and the foam exhaust line 7, strikes the surface of the gas-charged liquid in the reaction vessel 1 at an angle. The turbulence thus additionally generated at the surface, together with the impact forces present, leads to the destruction of the foam at the surface of the gas-charged liquid.

changer 14. This is accomplished by means of the jet device 25, which is operated with driving gas of high pressure via the driving-gas line 26 and draws in gas at low pressure via the gas supply line 27.

The charging of the liquid with gas in the reaction vessel 1 is accomplished by means of the liquid-gas jet device 15, which is arranged vertically in the upper part of the reaction vessel 1 and ends above the liquid surface in the reaction vessel 1. This liquid-gas jet device 15 is operated by means of the circulating liquid and draws in gas via the fresh-gas supply line 28 or, partly or completely, via the connecting line 29 from the central exhaust gas line 23. The gas and the circulating liquid are intimately mixed in the liquid-gas device 15 and are transferred into the liquid to be charged with gas in the reaction vessel with great momentum as a homogeneous liquid-gas jet. The gas bubbles contained in the liquid jet are embedded here deep in the liquid in the reaction vessel 1 and must rise through the entire height of the liquid to the surface in the turbulence area caused by the jet. This leads to favorable conditions for the material transfer of gas to liquid.

The gas escaping at the liquid surface of the reaction vessel 1 and that escaping from the gas separator 2 via the foam discharge line 17 is discharged into the atmosphere via the central exhaust gas line 23. However, this gas can also be sucked in, partly or completely, by the liquid-gas jet device 15 via the connecting line 29 and used over again to gas-charge the liquid in the reaction vessel 1. The liquid to be charged with gas can be fed into the reaction vessel 1 continuously or intermittently. It is also possible to carry out the charging of the liquid with gas in the reaction vessel 1 under overpressure.

Figure 2:
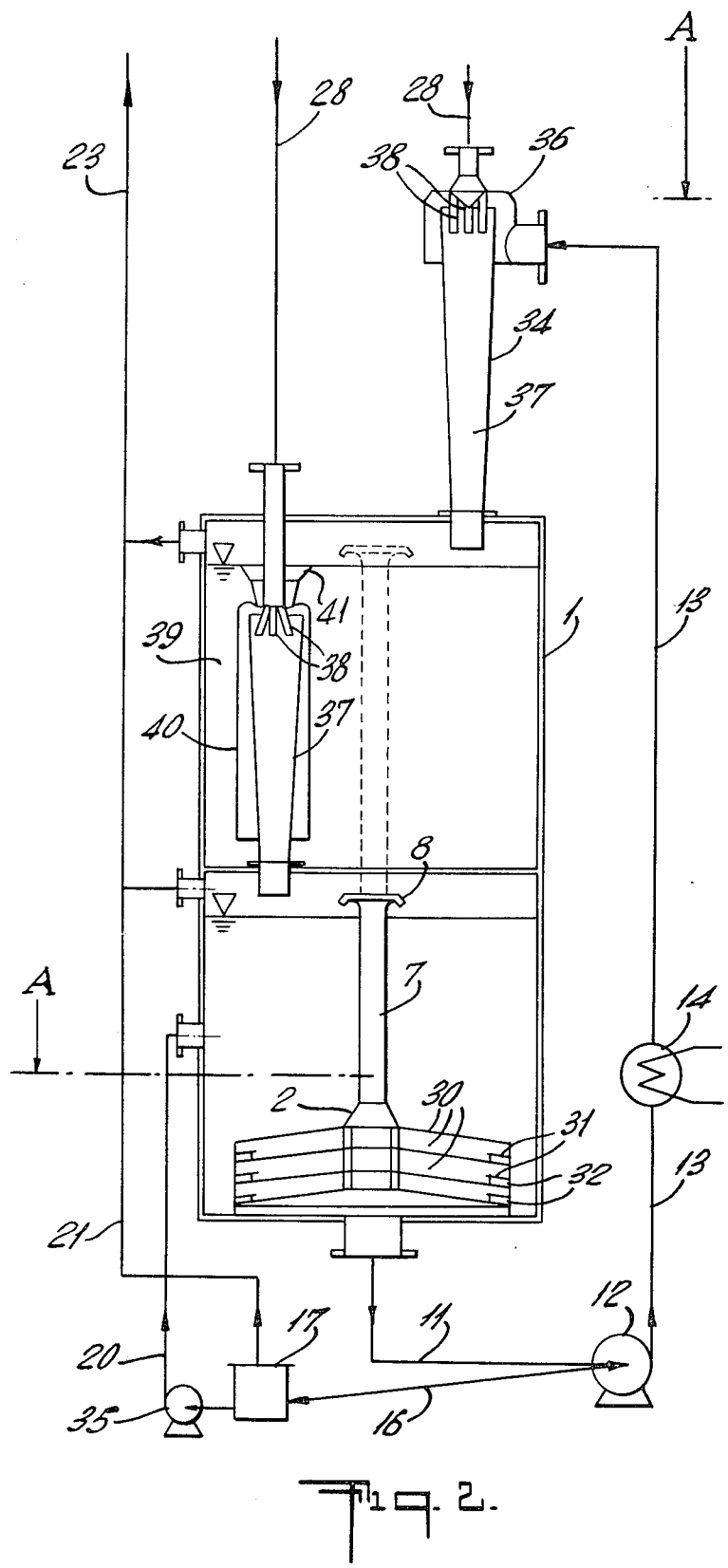
Figure 3:
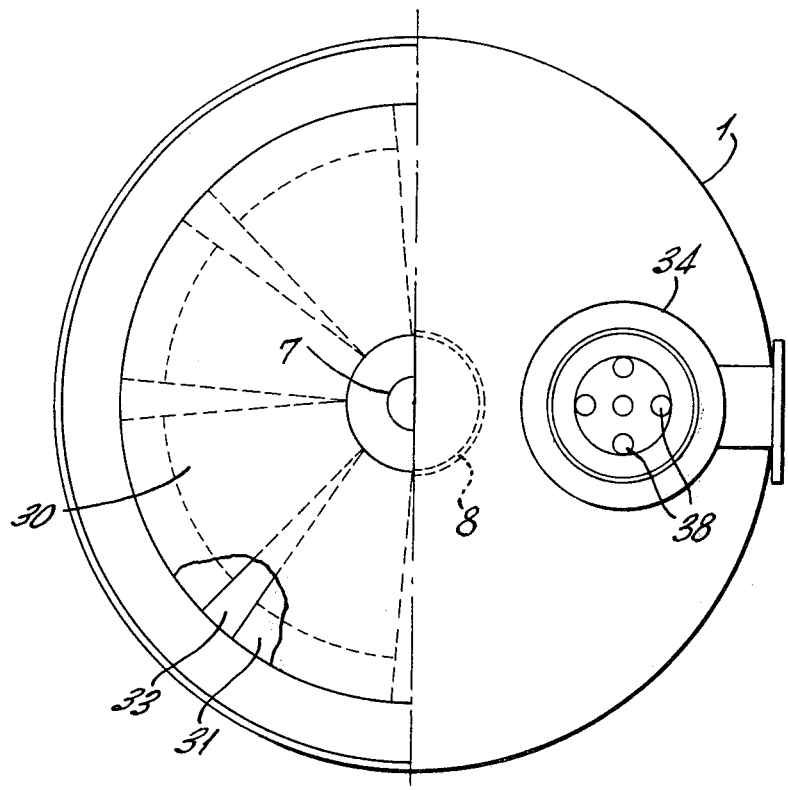

FIGS. 2 and 3 show a two-story reaction vessel 1 with well inflows 34, 39 as the gas-charging device in another embodiment of the invention. The heavily emulsified liquid flows from the lower story of the reaction vessel 1 to a gas separator 2, radially from the outside, which is arranged as in the example of the embodiment as per FIG. 1. This strongly emulsified liquid is separated into an emulsion with high gas content and a pre-degassed liquid. The emulsion with high gas content flows from the outside toward the inside through the interspaces of the conical guidance devices 30, which consist of individual segments, toward the foam discharge line 7, which is arranged centrally in the reaction vessel 1 and ends above the liquid level of one of the stories of the reaction vessel 1, and is equipped with a throttling device 8. The pre-degassed liquid flows, against the entrance direction, toward collecting pockets 31 arranged on the outside of the conical guidance devices 30 and from there, through the openings 32, on to the cavities 33 which are provided between the individual segments of the conical guidance devices 30. The pre-degassed liquid runs from the cavities 33 via the suction line 11 toward the degassing centrifugal pump 12 underneath the lowest conical guidance device 30. The centrifugal pump 12 pumps the liquid via the output line 13 and the heat exchanger 14 to the upper well inflow 34. At the same time, the liquid is further degassed in the centrifugal pump 12, utilizing the centrifugal forces in its rotor. The gas, which contains droplets of liquid and is separated in the rotor of the centrifugal pump 12 is fed to a liquid separator 17 via the venting line 16. The liquid accumulating in the liquid separator 17 is pumped back to the reaction vessel 1 by the volumetrically small pump 35 via the return line 20.

The gas accumulating in the liquid separator 17 is removed into the central exhaust gas line 23 via the exhaust gas line 21. The exhaust gas produced in the two stories of the reaction vessel 1 is also discharged to the atmosphere via the central exhaust gas line 23.

The liquid in the upper story of the reaction vessel 1 is charged with gas by the upper well inflow 34. The circulated liquid enters the well head 36 of the upper well inflow 34 via the pump line 13. From there, the liquid is plunged in free fall, without rotation, into the well pipe 37 and takes along in the process the gas, which is at atmospheric or higher pressure at the well head 36, via the gas input canals 38. The sucked-in gas and the circulated liquid are intimately mixed in the well pipe 37 and are transferred into the liquid of the upper story of the reaction vessel 1 with great momentum as a homogeneous liquid-gas jet.

The liquid in the lower story of the reaction vessel 1 is charged with gas via the lower well inflow 39. The main part of the liquid flows from the basin bottom of the upper story of the reaction vessel 1 toward the inlet of the well pipe 37 between the well pipe and the cylindrical skirt 40. From there, the liquid plunges in free fall, without rotation, into the well pipe 37 and takes along, for one, fresh gas via the fresh-gas supply line 28 and the gas supply canals 38 and, on the other hand, foam via the inlet funnel 41. The inlet funnel 41 can be provided with means for adjusting the size of the inlet cross section. In the well pipe 37 the sucked-in gas and the liquid are intimately mixed and transferred into the liquid of the lower story of the reaction vessel 1 with great momentum as a homogeneous liquid-gas jet.

We claim:

1. Apparatus for gasing liquids comprising a reaction vessel for containing liquid to be gassed, a separator element located within and towards the bottom of said vessel, said separator element constituting gravity operated means effective to separate medium in the separator into a primarily gaseous phase and a primarily liquid phase, a first conduit leading from a region of said separator at which said gaseous phase accumulates upwardly to a region of said vessel above the level of liquid therein, throttling means at the upper end of said first conduit means, second conduit means leading from a region of said separator at which said primarily liquid phase accumulates to a centrifugal pump disposed outside said vessel, said centrifugal pump having a central outlet for gas from said primarily liquid phase, third conduit means leading from said gas outlet to a second separator, fourth conduit means returning liquid from said second separator to said vessel above the level of liquid therein, said centrifugal pump having a peripheral outlet for liquid from said primarily liquid phase, fifth conduit means leading from said peripheral outlet to means disposed above the level of liquid in said vessel for entraining a gas in said liquid and for injecting said liquid and entrained gas into liquid in said vessel.

2. Apparatus as claimed in claim 1 wherein said means for entraining a gas in said liquid comprises an ejector pump means, said fifth conduit means being connected to said ejector pump means at a motive fluid inlet and a gas supply being connected to said ejector pump means at a pumped fluid inlet thereof.

3. Apparatus as claimed in claim 2 wherein said means for entraining a gas in said liquid is spaced from the surface of liquid in said vessel.

4. Apparatus as claimed in claim 2 including a gas exhaust line leading from an upper region of said vessel, said exhaust line being connected to a gas inlet of said means for entraining a gas in said liquid.

5. Apparatus as claimed in claim 1 wherein said means for entraining a gas in said liquid is spaced from the surface of liquid in said vessel.

6. Apparatus as claimed in claim 1 wherein said fourth conduit means includes an ejector pump means effective to draw liquid from said separator.

7. Apparatus as claimed in claim 6 wherein said fifth conduit means includes a branch connected to deliver motor fluid to said ejector pump means.

8. Apparatus as claimed in claim 1 wherein said fifth conduit means includes a pre-gas charging means between said centrifugal pump and said means for entraining a gas in said liquid.

9. Apparatus as claimed in claim 8, including a gas jet pump delivering gas to said pre-gas charging means.

10. Apparatus as claimed in claim 1 wherein said fifth conduit means includes a heat exchanger.

11. Apparatus as claimed in claim 1 wherein a gas outlet of said second separator is connected to a gas exhaust line leading from an upper part of said vessel.

12. Apparatus as claimed in claim 1 including a gas exhaust line leading from an upper region of said vessel, said exhaust line being connected to a gas inlet of said means for entraining a gas in said liquid.

13. Apparatus as claimed in claim 1 comprising a further reaction vessel, said vessels being disposed one above the other.

14. Apparatus as claimed in claim 1 wherein said separator element comprises a stack of generally conical elements, means defining an upper and central region in said separator at which a primarily gaseous phase accumulates, said first conduit means communicating with said region at the uppermost one of said conical elements, a manifold for said primarily liquid phase, and generally radially extending passage means leading to said manifold.

* * * * *